| United States Patent [19] | [11] Patent Number: 4,908,388 |
|---|---|
| Pickett et al. | [45] Date of Patent: Mar. 13, 1990 |

[54] BEHAVIOR MODIFYING COMPOUNDS

[75] Inventors: John A. Pickett; Ewen D. M. Macaulay, both of Hitchin, England

[73] Assignee: National Research Development Corporation, London, United Kingdom

[21] Appl. No.: 146,050

[22] Filed: Jan. 20, 1988

Related U.S. Application Data

[62] Division of Ser. No. 3,150, Jan. 14, 1987, Pat. No. 4,780,479, which is a division of Ser. No. 609,864, May 14, 1984, Pat. No. 4,657,926.

[30] Foreign Application Priority Data

May 21, 1983 [GB] United Kingdom ................ 8314521

[51] Int. Cl.$^4$ .................... A01N 33/18; A01N 33/24; C07C 48/30
[52] U.S. Cl. .................................. 514/716; 514/520; 514/521; 514/532; 514/533; 514/568; 514/569; 514/617; 514/646; 514/656; 514/721; 558/411; 558/423; 564/161; 564/183; 568/583; 568/586; 568/592

[58] Field of Search ...................... 568/592, 583, 586; 514/716, 721, 520, 521, 532, 533, 656, 568, 716, 569, 617, 646; 558/411, 423; 564/161, 183

[56] References Cited

U.S. PATENT DOCUMENTS 3,922,287 11/1975 Pawson ............................... 568/592

FOREIGN PATENT DOCUMENTS 2140421 11/1984 United Kingdom .

OTHER PUBLICATIONS

Liu et al., Chem ABS, 101, 1984, 151619p.
J. Chem. Ecol., 1984, 10(5)809–22.

*Primary Examiner*—Howard T. Mars
*Attorney, Agent, or Firm*—Oblon, Spivak, McClelland, Maier & Neustadt

[57] ABSTRACT

Derivatives of carbonyl-group containing behavior modifying compounds, in which said carbonyl group has been converted to a photolabile group which regenerates the carbonyl group on exposure to radiation, are of value in various methods for the control of animal, and in particular insect, species.

28 Claims, No Drawings

BEHAVIOR MODIFYING COMPOUNDS

This is a division, of application Ser. No. 07/003,150, filed Jan. 14, 1987 now U.S. Pat. No. 4,780,479 which is a division of application Ser. No. 06/609,864, filed May 14, 1984 now U.S. Pat. No. 4,657,926.

This invention relates to pheromones and like behaviour modifying compounds and is particularly concerned with the stabilisation of compounds of this type.

A pheromone may be defined, in the sense in which the term is used herein, as a substance which is secreted and released by an organism for detection and response by another organism of the same species. Many suggestions have been made concerning the use of pheromones in managing both pests and beneficial organisms. However, difficulties can arise in putting these suggestions to practical effect by virtue of the instability of many pheromones, particularly pheromones containing carbonyl groups. Thus, for example, sex attractant pheromones of many lepidopteran pests include long chain aliphatic aldehydes, such as (Z)-11-hexadecenal (I) that is secreted by *Plutella xylostella, Heliothis armigera, Heliothis zea* and many other species, which are difficult to use in control regimes in field crops because of their rapid aerial oxidation. The problems of aerial oxidation are complicated by the high volatility of low molecular weight aldehyde pheromones such as (E)-citral (II), which is an important component of the honey bee Nasonov pheromone that shows promise as a means of capturing honey bee swarms and for attracting honey bees to plants, which by enhancing the efficiency of pollination may increase the crop yield.

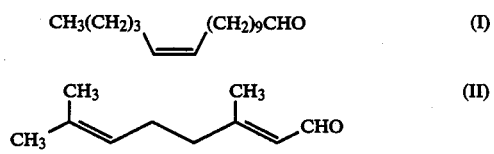

Although most ketones are relatively stable to aerial oxidation, field use is difficult for those with very high volatility such as heptan-2-one, which is a component of the honey bee mandibular gland pheromone and is of potential use in repelling honey bees from crops such as oilseed rape during pesticide treatment.

Proposals have been made in the past, for example in European patent application No. 82103961.7-published as 0066113, for overcoming the problems posed by the instability of carbonyl group-containing pheromones through the formation of bisulphite derivatives thereof which will regenerate the pheromone on hydrolysis. However, such derivatives present problems due to the variable effect of the pH of the environment upon release of the pheromone, particularly if the derivative is applied to a crop rather than being used in a lure.

It is an object of the present invention to provide a method of protecting pheromones, and like behaviour modifying compounds, through derivative formation which is applicable to any pheromone containing a carbonyl group to provide a propheromone which will release the pheromone in the field under various circumstances in a much more controlled manner than is the case with bisulphite derivatives. Moreover, it is possible by variation of the exact nature of the derivative to achieve some selection of the rate at which the pheromone is released.

Accordingly, the present invention comprises a derivative of a carbonyl group-containing behaviour modifying compound, as defined hereinafter, in which said carbonyl group has been converted to a photolabile group which regenerates the carbonyl group on exposure to radiation.

The term "behaviour modifying compound" is used herein firstly to cover any compound which, in nature, is secreted by an organism which can influence the behaviour or development of a receiving organism, this receiving organism more usually but not always being of the same species as the secreting organism. The compound may be secreted by a plant but most interest centres on compounds secreted by animal species, particularly by invertebrates and especially by various insect species, the term "insect" being used herein in its broad popular sense so that it includes within its scope members of the class Insecta but is not restricted thereto. "Behaviour-modifying compound" thus includes within its scope pheromones, and also allomones (where the compound is for detection and response by an organism of another species with advantage to the releasing organism) and kairomones (where the compound is for detection and response by an organism of another species with advantage to the receiving organism). It will be appreciated, however, that the term "behaviour modifying compound" is wider than a combination of the terms pheromone, allomone and kairomone in that, for example, it extends to compounds which are secreted but are not necessarily released and thus unequivocally includes compounds such as polygodial. Certain behaviour modifying compounds may be obtained from more than one natural source, for example certain insect pheromones also being obtainable from plants. Moreover, although any compound included by the first part of the definition of a "behaviour modifying compound" must necessarily have an occurrence in nature, the carbonyl group-containing compound from which the derivative is obtained may be either from a natural source or synthetic.

The term "behaviour modifying compound" is used herein secondly to cover compounds which are analogues and/or isomers of said naturally occurring compounds covered by the first part of the definition and which retain the carbonyl group thereof intact and exhibit the same or a modified influence on the behaviour or development of an organism. Most commonly, the organism influenced will be the same as that influenced by the parent compound and the influence will more usually be of the same rather than a modified type. It will be appreciated that such analogues and/or isomers may either occur naturally or be produced synthetically. If the analogue and/or isomer does occur in nature, it will of course already be encompassed by the first part of the definition of a "behaviour modifying compound". As regards such analogues and isomers, the analogues usually comprise a hydrocarbon moiety which (i) is a lower or higher, unbranched or branched homologue of the hydrocarbon moiety of the pheromone and/or (ii) contains a greater or lesser number of sites of carbon to carbon unsaturation as compared therewith, whilst the isomers usually involve one or more modifications as follows: (i) they have one or more sites of carbon to carbon unsaturation in different position(s) from the position(s) in the natural compounds; (ii) they are structural isomers involving a different position for the carbonyl group and/or involving a different arrangement of branching or lack of branching therein; (iii) they are geometrical isomers having different configuration(s) at carbon-to-carbon double bond(s); and, less usually, (iv) they are optical isomers, including both enantiomers and diasteroisomers, of the natural compound.

In many cases the behaviour modifying compound will comprise a saturated or particularly an unsaturated aliphatic hydrocarbon in which two hydrogen atoms attached to a carbon atom thereof are replaced by an oxo group. Moreover, in many cases the compound will be effective against an insect or insects. Examples of specific behaviour modifying compounds to which the present invention may be applied are the following pheromones, the insects of particular interest from which they may be obtained, and upon which they exert a behaviour modifying effect also being indicated.

Heptan-2-one
*Apis mellifera.*
(E)-2,7-Dimethyl-2,6-octadienal (citral)
*Apis mellifera.*
Undecanal
*Gallena mellenella*
(Z)-9-tetradecenal
*Heliothis virescens, Heliothis zea, Plutella xylostella* and *Prays oleae.*
(Z)-11-Tetradecenal
*Choristoneura fumiferana* and *Heliothis armigera.*
(E)-11-Tetradecenal
*Choristoneura fumiferana.*
Hexadecanal
*Heliothis armigera, Heliothis virescens* and *Heliothis zea*
(Z)-7-Hexadecanal
*Heliothis zea, Prays citri*
(Z)-8-Hexadecenal
*Trogoderma granarium.*
(Z)-9-Hexadecenal
*Heliothis armigera, Heliothis virescens* and *Heliothis zea.*
(Z)-11-Hexadecenal
*Chilio suppressalis, Heliothis armigera, Heliothis virescens, Heliothis zea* and *Plutella xylostella.*
(Z)-13-Octadecenal
*Chilio suppressalis.*

It will be appreciated that, where desired, a mixture of behaviour modifying compounds may be used in photolabile derivative form, for example two or more of the aldehydes indicated above as being present in the tobacco bud worm, *H. virescens*, the corn ear worm, *H. zea*, or the rice stem borer, *C. suppressalis* may be used together. Among the specific behaviour modifying compounds listed above, of particular interest are heptan-2-one and (E)-citral in conjunction with management of the honey bee, *A. mellifera* (L.), and especially (Z)-11-hexadecenal in conjunction with control of the diamond back moth. *P. xylostella* (L.).

In preferred types of photolabile derivative according to the present invention the carbonyl group is converted into an adduct formed with an alcohol (being either an acetal or a ketal depending on whether the behaviour modifying compound is of the aldehyde or ketone form), the adduct being convertible back to the carbonyl group on exposure to radiation (ultra-violet and/or visible). Among various suitable adducts of this type, those based upon benzyl alcohol and containing a moiety

which may optionally be ring substituted, are of particular interest. Of the several possible types of such benzyl alcohol based adducts, two particular types may conveniently be used. These consist of acetals or ketals in which the adduct is formed between the carbonyl compound and two molecules of benzyl alcohol or ring substituted benzyl alcohol and acetals and ketals in which the adduct is formed between the carbonyl compound and one molecule of a 1-phenyl- or 1,2-diphenyl-substituted ethylene glycol (1,2-ethane diol) or a similar compound which is ring substituted. Particularly preferred adducts thus have the formulae (III), (IV) and (V)

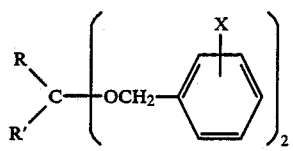

(III)

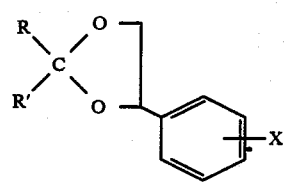

(IV)

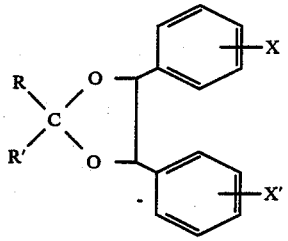

(V)

wherein RR'C< represents the residue of the behaviour modifying compound RR'C=O (R' being H when the compound is an aldehyde and an organic group when it is a ketone), and X and X' each separately represent hydrogen or one or more organic substituent groups.

A wide variety of types of substituent groups X and X' may be used including most particularly nitro but also halogen groups, for example fluoro, chloro and bromo, alkoxy groups including those containing $C_{1-5}$ alkyl groups and especially methoxy, alkyl groups, for example $C_{1-5}$ groups and especially methyl, cyano, and carboxy and groups derived therefrom such as amide and particularly ester groups, for example those formed with $C_{1-5}$ alkanols. Another type of substituent X or X' is one or more fused benzene rings or substituted benzene rings, which may for example be substituted as just described. Thus, the adduct may for example contain a napthyl or phenanthryl group or two of such groups, although adducts (V) containing two such group may be somewhat bulky.

The value of using adducts which contain a group X or groups X and X' which are other than hydrogen lies in the possibility, where this is desirable, of either increasing or decreasing the photolability of the adduct as compared with that which is unsubstituted, although the unsubstituted adducts are of course generally the most accessible. Various substituents may alter the photolability of the adduct in various ways. Firstly, there is the specific case of a nitro group at the ortho position of the ring which will enhance the photolability of the adduct due to an interaction between the nitro group and the adjacent benzyl carbon atom which assists the abstraction of a hydrogen atom from this carbon atom which occurs on irradiation as the first step in the breakdown of the adduct. Secondly, there is the general case of groups which withdraw electrons from or release electrons into the ring, and may thereby have an effect on photolability. In general, withdrawal and release will respectively decrease and increase photolability, although it will be appreciated that the effect will depend on the position of substitution according to the usual tenets of aromatic substitution. Thirdly, there is the general case of groups which extend the conjugation already provided by the benzene ring and thus increase the chromophoric nature of the adduct thereby enhancing its degree of photolability to visible as opposed to ultra violet radiation.

Groups of particular interest for producing an enhancement of photolability are thus particularly o-nitro but also m-alkoxy, especially m-methoxy, so that compounds according to the present invention of particular interest are those of formulae (III), (IV) and (V) in which X, or X and X' (which more usually represent the same pattern of substitution by the same substituents) represent two or especially one o-nitro group or one or especially two m-methoxy groups. It will be appreciated, however, that, depending on the nature of the residue RR'C< and the particular use being made of the compound, less photolabile compounds (III), (IV) and (V) in which X represents hydrogen or p-nitro may be of especial value. Groups of particular interest for producing an enhancement of photolability to visible light are cyano, carboxyl and groups derived therefrom, and also a fused benzene ring or rings.

It is of course possible to use other forms of adduct than those represented by the formulae (III), (IV) and (V). Alternatives which may be considered based on a moiety

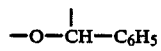

or such a ring substituted moiety are analogues of the adducts of type (III) having additional phenyl group or substituted phenyl group attached to the

group. It is also possible to use adducts incorporating other types of photolabile group described in the art which are susceptible to the formation of an adduct with a carbonyl group, but the types of adduct described specifically above have been found to be well suited to the formation of photolabile compounds from carbonyl-group containing behaviour modifying compounds.

Specific examples of compounds according to the present invention are listed below, the identifying symbols included in brackets being those used hereinafter in Tables 1 and 2.

(Z)-1,1-dibenzoxyhexadec-11-ene (Ic)
(Z)-1,1-di-o-nitrobenzoxyhexadec-11-ene (Id)
(Z)-1,1-bis(3',5'-dimethoxybenzoxy)-hexadec-11-ene (Ie)
(E)-1,1-dibenzoxy-3,7-dimethylocta-2,6-diene (IIc)
(E)-1,1-di-o-nitrobenzoxy-3,7-dimethylocta-2,6-diene (IId)
(E)-1,1-bis(3',5'-dimethoxybenzoxy)-3,7-dimethylocta-2,6-diene (IIe)
2.2-dibenzoxyheptane (IIIc)
2.2-di-o-nitrobenzyxyheptane (IIId)
2.2-bis-(3',5'-dimethoxybenzoxy)-heptane (IIIe)
2-[(Z)-10'-pentadecenyl]-4-(o-nitrophenyl)-1,3-dioxolane (If)
2-[(Z)-10'-pentadecenyl]-4-(p-nitrophenyl)-1,3-dioxolane (Ig)
2-[(E)-2',6'-dimethylhepta-1',5'-dienyl]-4-(o-nitrophenyl)-1,3-dioxolane (IIf)
2-[(E)-2',6'-dimethylhepta-1',5'-dienyl]-4-(p-nitrophenyl)-1,3-dioxolane (IIg)
2-methyl-2-pentyl-4-(o-nitrophenyl)-1,3-dioxolane (IIIf)
2-methyl-2-pentyl-4-(p-nitrophenyl)-1,3-dioxolane (IIIg)

The procedures used in the preparation of the preferred compounds of formulae (III) to (V) will vary in detail according to the nature of the alcohol or glycol used as well as that of the carbonyl containing behaviour modifying compound. Some comments may, however, be made by way of guidance. These adducts based upon benzyl alcohol are in some cases difficult to prepare directly so that (Z)-11-hexadecenal has been found to react with benzyl alcohol or substituted benzyl alcohols in the presence of p-toluene sulphonic acid (TSOH) to give acetals in only low yield, whilst (E)-citral gave acetals together with many by-products and heptan-2-one could not be induced to react. A preferred process for the formation of such adducts involves "transacetalization" of the acetal of ketal formed with an aliphatic alcohol such as ethanol or another alcohol containing an alkyl group, particularly a $C_{1-5}$ unbranched alkyl group, such tranacetalization generally proceeding smoothly with good yield in the presence of a small amount of an acid catalyst. Thus, the diethyl acetal of (Z)-11-hexadecenal and the diethyl ketal of heptan-2-one react readily with benzyl alcohols in the presence of p-toluene sulphonic acid, but care is required in the latter instance since with o-nitrobenzylalcohol, for example, the o-nitrobenzyl vinyl ether is formed if the reaction time is too long. The transacetalization of the diethylacetal of (E)-citral and the benzyl alcohols is conveniently effected in the presence of the weaker catalyst, ammonium chloride, instead of p-toluene sulphonic acid in order to obviate cyclization of the terpenoid structure.

((Z)-11-hexadecenal is readily acetalized directly in good yield with, for example, o- or p-nitrophenyl ethylene glycol in the presence of p-toluene sulphonic acid. In contrast, (E)-citral with the catalyst oxalic acid and heptan-2-one with p-toluene sulphonic acid gave the dioxolane adducts in only low yield. However, the transacetalization of, for example, the diethyl acetal of (E)-citral and o- or p-nitrophenylethylene glycol is readily carried out with ammonium chloride and the transacetalization of, for example, the diethyl ketal of heptan-2-one and o- or p-nitrophenyl ethylene glycol is readily effected without a catalyst.

Procedures for the preparation of acetals and ketals from aliphatic alcohols such as ethanol and for the preparation of the phenyl ethylene glycol reactants are illustrated hereinafter in the Examples. The diphenyl ethylene glycols, for use as intermediates in the preparation of adducts of type (V) and in which intermediates each oxy group carries a hydrogen atom rather than being linked by a group RR'C< as in (V), may conveniently be prepared from the corresponding stilbene. The double bond of the stilbene is dihydroxylated either directly using an oxidising agent such as cold, dilute, neutral potassium permanganate or peroxyfomic acid, or through the intermediate formation of an epoxide, for example by the use of aqueous bromine to give a bromohydron followed by alkali or by the use of peroxybenzoic acid, the epoxide then being subjected to acid hydrolysis.

It will be appreciated that the preparation of photolabile adducts according to the present invention may, however, be carried out by modifications of the above described procedures and also by alternative procedures, as will be apparent to those skilled in the art.

The compounds according to the present invention may be used with the object of stabilising behaviour modifying compounds and/or providing a controlled slow release thereof in a wide variety of contexts, including direct application to a crop. The invention is of particular application, for both monitoring and direct control, to invertebrates and especially to insects, although not of course being restricted thereto, specific invertebrates other than insects being, for example, molluscs such as slugs and nematodes.

Attractant compounds, for example sex pheromones, may be used for the attraction of pests to a site for the purpose of monitoring or for their destruction, this being an approach of general applicability which has been described in some detail in relation to various mosquito species in UK Patent Application No. 8230149, to be published as GB No. 2111481A. Alternatively, attractant compounds may be used in the collection of beneficial insects or their attraction to sites where they will exert their beneficial effect, this approach having been described in relation to the honey bee in UK Patent Application No. 8206254, published as GB No. 2095998A. Yet a further approach involves the use of repellent compounds either to discourage beneficial insects from visiting a site where they may suffer harm, for example from pesticides, or, in the case of pests, to prevent damage to a crop due to feeding thereon or virus transmission thereto. Repellent compounds may also find use in dispersing pests to enhance their contact with pesticides. Such general approaches with repellent compounds are described in the context of beneficial insects in relation to the honey bee in a paper by Free and Ferguson in the Journal of Agricultural Science, Cambridge (1980, 94, 151), and in the context of pests in relation to aphids in UK Patent Application No. 8215628, published as GB No. 2106503A.

It will be appreciated from the foregoing references that the derivatives according to the present invention will usually be employed in the form of a composition comprising the derivative together with a solid or liquid carrier with which the derivative may be integral or non-integral, an example of an integral composition being a liquid spray for application to crops, etc., and an example of a non-integral composition being certain types of insect lure such as a closure of plastics material.

Specific applications of the present invention involve the use of photolabile derivatives of (E)-citral and heptan-2-one in connection with honey bees in contexts outlined previously and, especially, the use of photolabile derivatives of (Z)-11-hexadecenal in the attraction and destruction of the diamond back moth (*Plutella xylostella*) and of other insects which secrete this compound such as *Heliothis armigera*, for example by the use of lures incorporating pesticide or by the separate application of a pesticide. The sex attractant pheromone of the diamond back moth comprises mainly (Z)-11-hexadecenal and (Z)-11-hexadecenyl acetate. Tests with sticky traps containing (Z)-11-hexadecenyl acetate and a photolabile derivative of (Z)-11-hexadecenal have shown good catches over four weeks comparable to those obtained in nearby tests using (Z)-11-hexadecenal and (Z)-11-hexadecenyl acetate as a lure, which latter type of lure must however be replaced during the course of the four weeks as it will not maintain its level of attractancy for more than two weeks, at the most, owing to aerial oxidation of the aldehyde.

The present invention thus further includes a method of influencing the behaviour of a member of an animal species, particularly an insect, which comprises applying to a selected locus a derivative of a carbonyl-group containing behaviour modifying compound as described hereinbefore.

The invention is illustrated by the following Examples.

EXAMPLE 1

Preparation of dibenzyl and substituted dibenzyl acetals and ketals

(1) Diethyl acetals and ketals

The aldehyde or ketone (100 mmol), triethylorthoformate (125 mmol) and absolute ethanol (40 ml) are mixed together. The catalyst (200 mg) is added and the mixture stirred at room temperature under nitrogen for 24 hours. The reaction is monitored by gas-liquid chromatography on a 5'×0.25" glass column of 10% OV-17 on Chromosorb W at 170° C. with a 20 ml/minute $N_2$ flow. The ethanol is removed under vacuum, hexane (200 ml) is added and the solution is partitioned with saturated aqueous $NaHCO_3$ solution and the hexane layer removed and dried over $Na_2CO_3$. After removing the solvent, the residual oil is vacuum distilled to give the required diethyl acetal or ketal.

(2) Dibenzyl and substituted dibenzyl acetals and ketals

The diethyl acetal or ketal (10 mmol) and benzyl alcohol or substituted benzyl alcohol (30 mmol) in benzene (100 ml) are heated slowly with catalyst and the benzene-ethanol azeotropic mixture is distilled out until the temperature reaches the boiling point of benzene. The reaction mixture is then cooled, basified with anhydrous $K_2CO_3$ and concentrated. The residue is vacuum distilled to remove the excess alcohol (in the case of benzyl alcohol) or extracted with hexane several times (in the case of substituted alcohols such as o-nitrobenzyl alcohol or 3,5-dimethoxybenzyl alcohol). The residue from the vacuum distillation or the hexane extraction concentrate is purified on an alumina column, eluting with hexane containing gradually increasing amounts of ether. The appropriate fractions are combined and evaporated to give the required dibenzyl or substituted dibenzyl acetal or ketal.

The diethyl acetal or ketal is prepared by the above general procedure from (Z)-11-hexadecenal, (E)-and (Z)-citral in admixture and heptan-2-one using NH$_4$Cl as catalyst in the first two cases and TsOH in the last. (Z)-1,1-Diethoxyhexadec-11-ene is obtained in 61.5% yield and has a b.p. 118°–120° C./0.05 mm, $n_D^{20}$ 1.4475; (E)-and (Z)-1,1-diethoxy-3,7-dimethoxyocta-2,6-diene in admixture are obtained in 83.6% yield and have b.p. 68°–70° C./0.2 mm, $n_D^{20}$ 1.4511; 2,2-diethoxyheptane is obtained in 71% yield and has b.p. 88°–92° C./18 mm.

The details of the "transacetalisation" reactions effected between the above three products and each of benzyl alcohol, o-nitrobenzyl alcohol and 3,5-dimethoxybenzyl alcohol are given in Table 1, the products being designated by the FIGS. 1, II or III according to the carbonyl compound involved and by the letters c, d or e according to the alcohol involved. The catalyst used was an amount selected in the range of 3–100 mg of p-toluene sulphonic acid for all of the products of types I and III, 100 mg of ammonium chloride for products II and IId and 100 mg of oxalic acid for product IIe.

STARTING MATERIALS (1) Carbonyl compounds (Z)-11-Hexadecenal is prepared from (Z)-11-hexadecenol which is obtained from 11-hexadecynol (this being obtained in turn by the reaction of 10-bromodecan-1-ol and 1-hexyne), the procedure being based on that of Nesbitt et al, J. Insect Physiol., 1975, 21, 1983. (E)-citral in admixture with ca. 40% of (Z)-citral, and heptan-2-one are obtained commercially.

(2) Benzyl alcohols

All three are obtained commercially.

containing gradually increasing amounts of ether. The appropriate fractions are combined and evaporated to give the required product.

Method B

The diethyl acetal or ketal (10 mmol) and o- or p-nitrophenylethylene glycol (15 mmol) in benzene (100 ml) are heated slowly either without or with catalyst (100 mg) and the benzene-ethanol azeotropic mixture is distilled out until the temperature reaches the boiling point of benzene. The reaction mixture is cooled, basified with anhydrous K$_2$CO$_3$ and concentrated. The residue is extracted with hexane several times and the hexane extracts are chromatographed on an Al$_2$O$_3$ column, eluting with hexane containing gradully increasing amounts of ether. The appropriate fractions are combined and evaporated to give the required product.

The details of the 1,3-dioxolane preparations effected by the above general procedure A for (Z)-11-hexadecenal and the above general procedure B for (E)- and (Z)-citral in admixture (with a NH$_4$Cl catalyst) and for heptan-2-one (with no catalyst) and each of o-nitrophenylethylene glycol and p-nitrophenylethylene glycol are given in Table 2, the products being designated by the FIGS. 1, II or III according to the carbonyl compound involved and by the letters f or g according to the glycol involved. The 1,3-dioxolanes derived from (Z)-11-hexadecenal and heptan-2-one are a mixture of two diastereoisomers whilst those derived from (E)-citral in admixture with (Z)-citral are a mixture of four isomers.

STARTING MATERIALS (1) Carbonyl compounds

These or the diethyl acetal or ketal derived therefrom are obtained as described under Example 1.

TABLE 1

Dibenzyl and substituted dibenzyl acetals and ketals

| Product | Carbonyl compound from which diethyl acetal or ketal is derived | Alcohol | Yield of adduct % | Refractive index of adduct $n_D$ |
|---|---|---|---|---|
| Ic | (Z)-11-Hexadecenal | Benzyl alcohol | 98.3 | 1.5088 (20° C.) |
| Id | (Z)-11-Hexadecenal | o-Nitrobenzyl alcohol | 95.1 | 1.5271 (20° C.) |
| Ie | (Z)-11-Hexadecenal | 3,5-Dimethoxybenzyl | 82.8 | 1.5122 (20° C.) |
| IIc | (E)- and (Z)-Citral | Benzyl alcohol | 88.6 | 1.5281 (20° C.) |
| IId | (E)- and (Z)-Citral | o-Nitrobenzyl alcohol | 83.1 | 1.5406 (20° C.) |
| IIe | (E)- and (Z)-Citral | 3,5-Dimethoxybenzyl alcohol | 82.6 | 1.4528 (19° C.) |
| IIIc | Heptan-2-one | Benzyl alcohol | 78.8 | 1.5429 (19.5° C.) |
| IIId | Heptan-2-one | o-Nitrobenzyl alcohol | 74.6 | 1.5429 (19.5° C.) |
| IIIe | Heptan-2-one | 3,5-Dimethoxybenzyl alcohol | 29.2 | 1.5256 (19.5° C.) |

EXAMPLE 2

Preparation of 2-substituted-4-(o- or p-nitrophenyl)-1,3-dioxolanes

Method A

The aldehyde (2 mmol), o- or p-nitrophenylethylene glycol (4 mmol) and p-toluenesulfonic acid (20 mg) are dissolved in benzene (50 ml) and the solution is refluxed under nitrogen in a Soxhlet apparatus having the extraction thimble filled with dehydrated MgSO$_4$. The reaction is monitored by thin layer chromatography on silica gel, developing with hexane-ether. After six hours, the reaction mixture is cooled and the pricipitate filtered off. The filtrate is washed with saturated aqueous Na$_2$CO$_3$ followed by brine, and is then dried over MgSO$_4$. After removing the solvent the residue is chromatographed on Al$_2$O$_3$ (neutral), eluting with hexane (2) Glycols o- and p-Nitrophenylethylene oxide are prepared from o- and p-nitroacetophenone through brominaton, reduction and dehydrobromination according to Guss and Mautrier, J. Org. Chem. 1951, 16, 887 and Guss, ibid, 1952, 17, 678. The oxide (2.9 g, 17.6 mmol) and potassium carbonate (1.7 g) are dissolved in 50% aqueous 1,4-dioxane (130 ml). The reaction mixture is refluxed at 110° C. with magnetic stirring for 24 hours, the reaction being monitored by t.l.c. as described above. After cooling the reaction mixture is neutralized with 2N HCl, concentrated under vacuum, extracted with ether, and dried over MgSO$_4$. After removing the ether, the residue is crystallized from benzene-hexane to give, as light brown crystals, o-nitrophenylethylene glycol in 69.4% yield having m.p. 91°–92° C. or p-nitrophenylethylene glycol in 51.3% yield having m.p. 80°–92° C.

TABLE 2

| | 2-Substituted-4-(o- or p-nitrophenyl)-1,3-dioxolanes) | | | |
|---|---|---|---|---|
| Product | Carbonyl compound | Glycol | Yield of adduct % | Refractive index of adduct $n_D$ |
| If | (Z)-11-Hexadecenal | o-Nitrophenylethylene glycol | 73.3 | 1.5061 (18.5° C.) |
| Ig | (Z)-11-Hexadecenal | p-Nitrophenylethylene glycol | 99.3 | 1.5107 (18.5° C.) |
| IIf | (E)- and (Z)-Citral | o-Nitrophenylethylene glycol | 72.9 | 1.5358 (20° C.) |
| IIg | (E)- and (Z)-Citral | p-Nitrophenylethylene glycol | 85.8 | 1.5370 (20° C.) |
| IIIf | Heptan-2-one | o-Nitrophenylethylene glycol | 79.9 | 1.5150 (20° C.) |
| IIIg | Heptan-2-one | p-Nitrophenylethylene glycol | 93 | 1.5181 (16.5° C.) |

EXAMPLE 3

Comparison of the photolability of various compounds upon irradiation

Irradiation was carried out over a CAMAG universal HV lamp emitting at 350 nm. The compound to be irradiated was dissolved either in hexane or 80% aqueous dioxane and diluted to 1 mg/ml concentration, the sample then being sealed in a borosilicate glass tube under nitrogen. An irradiation time of 24 hours was employed for the experiment. The recovered carbonyl compounds were identified by co-injection with authentic samples and quantitatively analysed on gas-liquid chromatography using a 7'×0.25" glass colum of 10% carbowax on Chromosorb W at 200° C. for the detection of (Z)-11-hexadecenal, at 190° C. for the detection of (E)-citral and at 140° C. for the detection of 2-heptanone. In all cases studied, no carbonyl compounds were recovered from the control (which was wrapped with aluminium foil). Those samples more sensitive to UV were examined in hexane under a 20W daylight lamp over periods of from 3 to 24 hours.

The results obtained for the various adducts identified in Tables 1 and 2 are shown in Tables 3 and 4. It will be seen that no recovery of the carbonyl compound was detected in the case of the acetals and the ketal derived from benzyl alcohol, 3,5-dimethoxybenzyl alcohol and p-nitrophenylethylene glycol. However, if only small amounts of carbonyl compounds were formed during UV irradiation these would most likely be lost by photolysis and their release would be undetected. Such photolysis presumably accounted for the full theoretical yield not being observed for any of the released carbonyl compounds. Moreover, failure to achieve release under these conditions does not mean that the same adducts will not release the carbonyl compound over a longer period in the field and that a slower rate of release may not be more appropriate for practical use of the adducts in the field.

TABLE 3

| | Irradiation of adducts under UV (350 nm) lamp | |
|---|---|---|
| | Recovery of carbonyl compound after 24 hours % | |
| Adduct | in hexane | in 80% aqueous dioxane |
| Ic | 0 | 0 |
| IIc | 0 | 0 |
| IIIc | 0 | 0 |
| Id | 82 | 62 |
| IId | 74 | 41 |
| IIId | 91 | 89 |
| Ie | 19 | 12 |
| IIe | 0 | 0 |
| IIIe | 0 | 0 |
| If | 97 | 90 |
| IIf | 96 | 71 |
| IIIf | 87 | 82 |

TABLE 3-continued

| | Irradiation of adducts under UV (350 nm) lamp | |
|---|---|---|
| | Recovery of carbonyl compound after 24 hours % | |
| Adduct | in hexane | in 80% aqueous dioxane |
| Ig | 0 | 0 |
| IIg | 0 | 0 |
| IIIg | 0 | 0 |

TABLE 4

| | Irradiation of adducts under a daylight lamp | | | |
|---|---|---|---|---|
| | Recovery of carbonyl compounds (%) | | | |
| Adduct | 3 hours | 6 hours | 12 hours | 24 hours |
| Id | 13.91 | 20.22 | 38.94 | 52.66 |
| If | 10.76 | 20.67 | 44.34 | 63.99 |
| IId | 7.93 | 9.80 | 11.64 | 15.08 |
| IIf | 5.26 | 8.95 | 14.86 | 22.03 |
| IIId | 7.15 | 10.58 | 25.45 | 35.32 |
| IIIf | 11.33 | 17.70 | 33.26 | 43.43 |

EXAMPLE 4

Comparison of persistence of (Z)-11-hexadecenal and an adduct thereof

Comparison between the persistence of (Z)-11-hexadecenal release from the underivatised material and the adduct If of Table 2 on glass was studied employing a method similar to that of Baker et al, J. Chem. Ecol., 1980, 6, 749. Either (Z)-11-hexadecenal (0.10 mg, 0.42 μmol) or the adduct If of Table 2 (0.17 mg, 0.42 μmol) was dissolved in hexane (100 μl) and placed on a glass disc (16 mm), in duplicate. After irradiation (20W daylight lamp) for 17 hours each disc was suspended in a closed 250 ml round-bottomed flask for a further three hours irradiation. (Z)-11-hexadecenal released from the discs onto the inner walls of the flasks was quantified by washing the flasks with portions (10 ml) of hexane solution of octadecane (0.01 mg/ml) as internal standard and then analysing the concentrated washings by gas chromatography using a 5'×0.25" glass column of 10% OV-17 on Chromosorb W at 170° C. with a 20 ml/minute $N_2$ flow.

It was found that the adduct If continued to release (Z)-11-hexadecenal (0.9 μg, 9%, in three hours) after the initial irradiation of 17 hours, none of the compound being obtained from the underivatised sample after this period.

EXAMPLE 5

Field studies with (Z)-11-hexadecenal adducts

Lures were prepared from polyethylene closures (WP/5, Fisons) containing one of
(i) (Z)-11-hexadecenyl acetate (10 μg).

(ii) (Z)-11-hexadecenyl acetate (10 μg)+adduct Id of Table 1 (33 μg, equivalent to 15 μg of (Z)-hexadecenal).

(iii) (Z)-11-hexadecenyl acetate (10 μg)+adduct If of Table 2 (25 μg, equivalent to 15 μg of the aldehyde).

The lures were hung in brown cardboard traps (Oecos), triangular in cross section (side 100 mm, 176 mm long) with a removable sticky card base. The traps were placed horizontally in five groups of the three randomly arranged lure types in a N/W line with 15 m spacing and the traps aligned E/W in Brussels sprouts at crop height, 10 Jun. 1982, Bedfordshire, UK. Diamondback moths, *Plutella xylostella* (L)., were counted each week and the sticky card changed each week for four weeks.

The weekly catch from the total of five groups of traps for each type of lure are shown in Table 5.

TABLE 5

| | Catches of diamondback moths | | | |
|---|---|---|---|---|
| | Weekly catch | | | |
| Composition of Lure | week 1 | week 2 | week 3 | week 4 |
| (Z)-11-hexadecenyl acetate (HLA) | 0 | 1 | 5 | 3 |
| HLA + Id | 87 | 379 | 332 | 197 |
| HLA + If | 171 | 369 | 287 | 126 |

It will be seen that the acetate alone caught few moths but that when the adducts were employed with the acetate there were good catches which persisted for the four weeks of the test. These catches were of a similar magnitude to those obtained in nearby tests using fresh lures containing the equivalent amount of the underivatised aldehyde and the acetate, but whose attractancy did not persist for longer than two weeks.

In 1983, similarly good catches were obtained with lures of types (ii) and (iii) containing adducts Id and If, respectively. Additional experiments were carried out using lures containing instead one of the adducts Ic and Ie of Table 1 and Ig of Table 2, in each case in an amount equivalent to 15 μg of the aldehyde and together with 10 μg of (Z)-11-hexadecenyl acetate. The catches recorded with these three additional types of lure were relatively low, being less than 5% of the catches recorded with the lures containing the adducts Id and If. This result does, however, contrast with the zero recoveries reported for these adducts in Table 3. Moreover, when the amounts of the adducts Ic, Ie and Ig were increased tenfold, the catches increased to 30% (for Ic and Ie) and 15% (for Ig) of those obtained with 15 μg aldehyde equivalent amounts of the adducts Id and If, and the persistence of the adducts Ic, Ie and Ig was found to be greater so that catches continued to be recorded using the adducts Ic, Ie and Ig after they had ceased with the adducts Id and If.

We claim:

1. In a method for influencing insect behaviour by the application to a selected locus of an insect behaviour modifying compound containing a carbonyl group, the improvement which comprises using the said compound in the form of a photolabile derivative of formula

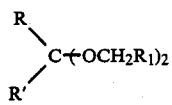

wherein RR'C< represents the residue of the carbonyl group-containing insect behaviour modifying compound being a divalent aliphatic hydrocarbon group of 7 to 18 carbon atoms, and $R_1$ represents an unsubstituted phenyl group, a phenyl group substituted by one or two substituents selected from the group consisting of nitro, halogen, alkoxy, alkyl, and amide and $C_{1-5}$ alkyl, ester, cyano, carboxy, groups of carboxy, or a phenyl group to which is fused a benzene ring which can be substituted by one or two of said substituents.

2. In the method of claim 1, the improvement which comprises using a photolabile derivative in which the grouping RR'C< derives from an insect pheromone or an isomer thereof which exhibits an influence on the behaviour of the said insect.

3. In the method of claim 1, the improvement which comprises using a photolabile derivative in which the grouping RR'C< derives from an insect pheromone.

4. In the method of claim 3, the improvement which comprises using a photolabile derivative containing a grouping RR'C< which is the residue of heptan-2-one or (E)-2,7-dimethyl-2,6-octadienal, said derivative being used to influence the behavior of honey bees.

5. In the method of claim 3, the improvement which comprises using a photolabile derivative containing a grouping RR'C< which is the residue of (Z)-11-hexadecenal, said derivative being used in the form of an insect lure to attract an insect which itself secretes (Z)-11-hexadecenal.

6. In the method of claim 5, the improvement in which the insect is *Plutella xylostella* or *Heliothis armigera*.

7. In the method of claim 1, the improvement which comprises using the said compound in the form of a photolabile derivative in which $R_1$ is phenyl or a phenyl group substituted by one or two substituents selected from nitro and $C_{1-5}$ alkoxy.

8. In the method of claim 7, the improvement which comprises using the said compound in the form of a photolabile derivative in which $R_1$ is phenyl, o-nitrophenyl, 1,5-dinitrophenyl, m-methoxyphenyl or 3,5-dimethoxyphenyl.

9. In the method of claim 1, the improvement which comprises using a photolabile derivative in which the grouping RR'C< derives from heptan-2-one, (E)-2,7-dimethyl-2,6-octadienal, (Z)-9-tetradecenal, (Z)-11-tetradecenal, (E)-11-tetradecenal, hexadecanel, (Z)-8-hexadecenal, (Z)-9-hexadecenal, (Z)-11-hexadecenal or (Z)-13-octadecenal.

10. In the method of claim 7, the improvement which comprises using a photolabile derivative in which the grouping RR'C< derives from heptan-2-one, (E)-2,7-dimethyl-2,6-octadienal or (Z)-11-hexadecenal.

11. In the method of claim 10, the improvement which comprises using a photolabile derivative in which $R_1$ is phenyl, o-nitrophenyl or 3,5-dimethoxyphenyl.

12. In the method of claim 1, the improvement which comprises using as the photolabile derivative (Z)-1,1-dibenzoxyhexadec-11-ene, (Z)-1,1-di-o-nitrobenzoxyhexadec-11-ene or (Z)-1,1-bis-(3',5'-dimethoxybenzoxy)-hexadec-11-ene.

13. A composition for influencing insect behaviour which comprises a photolabile insect behaviour modifying compound of formula

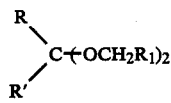

wherein RR'C< represents the residue of a carbonyl group-containing insect behaviour modifying compound, being a bivalent aliphatic hydrocarbon group of 7 to 18 carbon atoms, and $R_1$ represents an unsubstituted phenyl group, a phenyl group substituted by one or two substituents selected from the group consisting of nitro, halogen, alkoxy, alkyl, cyano, carboxy, and amide and $C_{1-5}$ alkly ester groups of carboxy, or a phenyl group to which is fused a benzene ring which can be substituted by one or two of said substituents, and an agriculturally suitable solid or liquid carrier with which the compound is integral or non-integral.

14. The composition according to claim 13, in which the grouping RR'C< derives from an insect pheromone or an isomer thereof which exhibits an influence on the behaviour of the said insect.

15. The composition according to claim 13, in which $R_1$ is phenyl or a phenyl group substituted by one or two substituents selected from nitro and $C_{1-5}$ alkoxy.

16. The composition according to claim 15, in which $R_1$ is phenyl, o-nitrophenyl, 1,5-dinitrophenyl, m-methoxyphenyl or 3,5-dimethoxyphenyl.

17. The composition according to claim 13, in which the grouping RR'C< derives from heptan-2-one, (E)-2,7-dimethyl-2,6-octadienal, (Z)-9-tetradecenal, (Z)-11-tetradecenal, (E)-11-tetradecenal, hexadecanal, (Z)-8-hexadecenal, (Z)-9-hexadecenal, (Z)-11-hexadecenal or (Z)-13-octadecenal.

18. The composition according to claim 17, in which the grouping RR'C< derives from heptan-2-one, (E)-2,7-dimethyl-2,6-octadienal or (Z)-11-hexadecenal and $R_1$ is phenyl, o-nitrophenyl or 3,5-dimethoxyphenyl.

19. The composition according to claim 13, in which the photolabile compound is (Z)-1,1-dibenzoxyhexadec-11-ene, (Z)-1,1-di-o-nitrobenzoxyhexadec-11-ene or (Z)-1,1-bis-(3',5'-dimethoxybenzoxy)-hexadec-11-ene.

20. The composition according to claim 13, in which the grouping RR'C< derives from an insect attractant, said composition having the form of an insect lure.

21. The composition according to claim 20, in which the grouping RR'C< derives from (Z)-11-hexadecenal.

22. A photolabile derivative of a carbonyl group-containing insect behaviour modifying compound having the formula

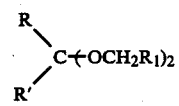

wherein RR'C< represents a bivalent aliphatic hydrocarbon group of 7 to 18 carbon atoms and $R_1$ represents an unsubstituted phenyl group, a phenyl group substituted by one or two substituents selected from the group consisting of nitro, halogen, alkoxy, alkyl, cyano, carboxy, and amide and $C_{1-5}$ alkyl ester groups of carboxy, or a phenyl group to which is fused a benzene ring which can be substituted by one or two of said substituents.

23. The derivative according to claim 22, in which $R_1$ is phenyl or a phenyl group substituted by one or two substituents selected from nitro and $C_{1-5}$ alkoxy.

24. The derivative according to claim 23, in which $R_1$ is phenyl, o-nitrophenyl, 1,5-dinitrophenyl, m-methoxyphenyl or 3,5-dimethoxyphenyl.

25. The derivative according to claim 22, in which the grouping RR'C< derives from heptan-2-one, (E)-2,7-dimethyl-2,6-octadienal, (Z)-9-tetradecenal, (Z)-11-tetradecenal, (E)-11-tetradecenal, hexadecanal, (Z)-8-hexadecenal, (Z)-9-hexadecenal, (Z)-11-hexadecenal or (Z)-13-octadecenal.

26. The derivative according to claim 22, in which the grouping RR'C< derives from heptan-2-one, (E)-2,7-dimethyl-2,6-octadienal or (Z)-11-hexadecenal and $R_1$ is phenyl, o-nitropyhenyl or 3,5-dimethoxyphenyl.

27. The derivative according to claim 22, which is (Z)-1,1-dibenzoxyhexadec-11-ene, (Z)-1,1-di-o-nitrobenzoxyhexadec-11-ene or (Z)-1,1-bis-(3',5'-dimethoxybenzoxy)-hexadec-11-ene.

28. The derivative according to claim 22, in which the grouping RR'C< derives from an insect pheromone or isomer thereof which exhibits an influence on the behaviour of the said insect.

* * * * *

UNITED STATES PATENT AND TRADEMARK OFFICE
CERTIFICATE OF CORRECTION

PATENT NO. : 4,908,388
DATED : March 13, 1990
INVENTOR(S) : John A. Pickett, et al.

It is certified that error appears in the above-identified patent and that said Letters Patent is hereby corrected as shown below:

Column 14, line 13, "alkyl, and amide and $C_{1-5}$ alkyl, ester,"

should read --alkyl, cyano, carboxy, and amide and $C_{1-5}$ alkyl ester-- line 14, delete "cyano, carboxy,"

line 55, "hexadecanel" should read --hexadecanal--.

Column 15, line 18, "alkly" should read --alkyl--.

Signed and Sealed this

Fifteenth Day of October, 1991

Attest:

HARRY F. MANBECK, JR.

*Attesting Officer*

*Commissioner of Patents and Trademarks*